(12) United States Patent
Lupien et al.

(10) Patent No.: US 7,245,063 B2
(45) Date of Patent: Jul. 17, 2007

(54) OPTIMIZED ULTRASONIC PHASED ARRAY TRANSDUCER FOR THE INSPECTION OF BILLET MATERIAL

(75) Inventors: Vincent Lupien, Wakefield, MA (US); Waled T. Hassan, Phoenix, AZ (US)

(73) Assignee: Honeywell International, Inc., Morristown, NJ (US)

( * ) Notice: Subject to any disclaimer, the term of this patent is extended or adjusted under 35 U.S.C. 154(b) by 361 days.

(21) Appl. No.: 10/987,707

(22) Filed: Nov. 12, 2004

(65) Prior Publication Data
US 2006/0103267 A1   May 18, 2006

(51) Int. Cl.
*H01L 41/08* (2006.01)
(52) U.S. Cl. ..................................... 310/334
(58) Field of Classification Search ................ 310/334, 310/369, 330, 311, 317, 316, 331; 73/598, 73/600, 620; 148/508, 671, 417; *H01L 41/08*
See application file for complete search history.

(56) References Cited

U.S. PATENT DOCUMENTS

| | | | |
|---|---|---|---|
| 4,431,936 A | 2/1984 | Fu et al. | |
| 5,099,459 A | 3/1992 | Smith | |
| 5,277,718 A * | 1/1994 | Paxson et al. ............. | 148/417 |
| 5,431,053 A | 7/1995 | Fink | |
| 5,513,532 A | 5/1996 | Beffy et al. | |
| 5,533,401 A * | 7/1996 | Gilmore ..................... | 73/620 |
| 5,549,002 A | 8/1996 | Howard et al. | |
| 5,948,985 A | 9/1999 | Brautigan et al. | |
| 6,202,489 B1 | 3/2001 | Beffy et al. | |
| 6,282,963 B1 | 9/2001 | Haider | |
| 6,318,178 B1 | 11/2001 | Kato et al. | |
| 6,393,916 B1 | 5/2002 | Bewlay et al. | |
| 6,401,537 B1 * | 6/2002 | Gigliotti et al. ............ | 73/598 |
| 6,543,272 B1 | 4/2003 | Vitek | |
| 6,613,004 B1 * | 9/2003 | Vitek et al. ................. | 601/2 |
| 6,789,427 B2 | 9/2004 | Batzinger et al. | |
| 2004/0050166 A1 | 3/2004 | Batzinger et al. | |

OTHER PUBLICATIONS

Ultra Sonic Phased Array Inspection of Titanium Billets( Review of Progress Quantitative Nondestructive Evaluation vol. 20 )2001 American Institue of Physics).*
Lupien, Vincent and Cancre, Fabrice, "Ultrasonic Phased Array Inspection of Titanium Billets," AIP Conf. Proced., 557(1) 919, (Apr. 30, 2001).

* cited by examiner

*Primary Examiner*—Darren Schuberg
*Assistant Examiner*—Karen Addison
(74) *Attorney, Agent, or Firm*—Ingrassia Fisher & Lorenz (57) ABSTRACT

An ultrasonic phased array transducer system comprises an ultrasonic phased array transducer having a piezo central element, concentric piezo ring elements enclosing the piezo central element, concentric sectored piezo rings having piezo sector elements enclosing the piezo ring elements; a driver/processor having a plurality of input/output ports, each input/output port in electrical communication with at least one of the piezo central element, the piezo ring elements, or the piezo sector elements; and a plurality of piezo element impedance matching circuits provided in a plurality of electrical channels connecting the driver/processor and the ultrasonic phased array transducer.

36 Claims, 8 Drawing Sheets

OPTIMIZED ULTRASONIC PHASED ARRAY TRANSDUCER FOR THE INSPECTION OF BILLET MATERIAL

BACKGROUND OF THE INVENTION

The present invention generally relates to ultrasonic transducers, and in particular to phased array ultrasonic transducers.

There continues to be a need for ever more sensitive detection of defects in structurally-critical metal components such as 8-inch titanium alloy or nickel alloy billets from which may be fabricated safety-critical rotating components used in turbine engines and other high-load, high-temperature applications. Ultrasound in the megahertz range is typically used for such inspection because of the ability to achieve relatively high defect resolution in such billets.

For example, U.S. Pat. No. 6,789,427B2 entitled "Phased array ultrasonic inspection method for industrial applications" discloses an inspection method which utilizes an array of transducers, which may be a linear array, to produce an ultrasonic transmission beam focused into a component undergoing inspection. U.S. Pat. No. 5,099,459 issued to Smith discloses a two-dimensional transducer array fabricated by segmenting a piezoelectric material of large elements into smaller elements. U.S. Pat. No. 4,431,936 issued to Fu et al. discloses transducer configurations, including linear arrays and concentric structures, for generating uniform and focused ultrasonic beams.

As can be seen, there continues to be a need for an improved ultrasonic apparatus and method for detecting small defects in billet material.

SUMMARY OF THE INVENTION

In one aspect of the present invention an ultrasonic phased array transducer system comprises an ultrasonic phased array transducer having a piezo central element with an active area, a concentric piezo ring element enclosing the piezo central element, the piezo ring element having an active area greater than the piezo central element active area, a concentric sectored piezo ring enclosing the piezo ring element, the sectored piezo ring having first and second piezo sector elements, the sectored piezo ring further having an active area greater than the piezo ring element active area; a driver/processor with a plurality of input/output ports; a first electrical channel connecting the piezo central element to a first input/output port in the driver/processor, the first electrical channel including a first impedance matching circuit functioning to match electrical characteristics of the piezo central element to the first input/output port; a second electrical channel connecting the piezo ring element to a second input/output port in the driver/processor, the second electrical channel including a second impedance matching circuit functioning to match electrical characteristics of the piezo ring element to the second input/output port; and a third electrical channel connecting the piezo sector element to a third input/output port in the driver/processor, the third electrical channel including a third impedance matching circuit functioning to match electrical characteristics of the piezo sector element to the third input/output port.

In another aspect of the present invention, an ultrasonic phased array transducer system comprises a housing; an ultrasonic phased array transducer attached to the housing to form a water-tight assembly, the ultrasonic phased array transducer having a piezo central element, a plurality of concentric piezo ring elements enclosing the piezo central element, a plurality of concentric sectored piezo rings enclosing the plurality of piezo ring elements, each sectored piezo ring having first and second piezo sector elements; a transducer control including a driver/processor having a plurality of input/output ports, a plurality of impedance matching circuits; a first electrical channel connecting the piezo central element to a first input/output port in the driver/processor, the first electrical channel including a first impedance matching circuit functioning to match electrical characteristics of the piezo central element to the first input/output port; a second electrical channel connecting the piezo ring element to a second input/output port in the driver/processor, the second electrical channel including a second impedance matching circuit functioning to match electrical characteristics of the piezo ring element to the second input/output port; and a third electrical channel connecting the piezo sector element to a third input/output port in the driver/processor, the third electrical channel including a third impedance matching circuit functioning to match electrical characteristics of the piezo sector element to the third input/output port.

In still another aspect of the present invention, an ultrasonic phased array transducer system comprises an ultrasonic phased array transducer having a piezo central element, nine concentric elliptical piezo ring elements enclosing the piezo central element, twenty concentric sectored piezo rings enclosing the nine piezo ring elements, each sectored piezo ring having at least four piezo sector elements; a driver/processor having a plurality of input/output ports; and a plurality of piezo element impedance matching circuits, each piezo element impedance matching circuit disposed in an electrical channel between an input/output port and a respective one of the piezo central element, the piezo ring elements, or the piezo sector elements.

In yet another aspect of the present invention, an ultrasonic phased array transducer comprises a piezo central element; and a plurality of concentric elliptical piezo ring elements enclosing the piezo central element, each piezo ring element having an area of approximately 43.2 mm$^2$, an area of approximately 105.1 mm$^2$, or an area in the range of approximately 43.2 mm$^2$ to approximately 105.1 mm$^2$.

In another aspect of the present invention, an ultrasonic phased array transducer suitable for use with a multi-channel driver/processor for inspecting a solid object comprises a piezo central element; nine concentric piezo ring elements enclosing the piezo central element, each piezo ring element having an area of from approximately 43.2 mm$^2$ to approximately 105.1 mm$^2$; sixteen concentric sectored piezo rings enclosing the nine piezo ring elements, each of the sixteen sectored piezo rings having four piezo sector elements, each of the four piezo sector elements having an area of from approximately 28.6 mm$^2$ to approximately 168.1 mm$^2$; two concentric sectored piezo rings enclosing the nine piezo ring elements, each of the two sectored piezo rings having six piezo sector elements, each of the six piezo sector elements having an area of from approximately 132.0 mm$^2$ to approximately 168.2 mm$^2$; an elliptical sectored piezo ring having eight piezo sector elements enclosing the nine piezo ring elements, each of the eight piezo sector elements having an area of approximately 169.0 mm$^2$; and an elliptical sectored piezo ring having sixteen piezo sector elements enclosing the nine piezo ring elements, each of the sixteen piezo sector elements having an area of approximately 176.9 mm$^2$.

In still another aspect of the present invention, an ultrasonic phased array transducer system comprises: an ultrasonic phased array transducer with a plurality of transducer piezo elements having a range of active area values; a driver/processor having a plurality of input/output ports; a plurality of electrical channels disposed between the plurality of transducer piezo elements and the plurality of input/output ports such that each input/output port is in electrical communication with at least one transducer piezo element; a baseline range of acceptable active area values derived from a listing of the active area values;and active area impedance matching circuitry for one or more of the electrical channels such that each input/output port in electrical communication with a corresponding transducer piezo element sees an active area value lying within the baseline range of acceptable area values.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention generally provides an apparatus and method for detecting internal defects in structurally-critical metal components. In particular, the apparatus may comprise an ultrasonic transducer that can produce a 40-mil spot size at depths ranging from 0.2 to 4.5 inches, a range which allows for inspection of components such as an 8-inch diameter Ti-6A-4V billet with a single ultrasonic transducer. Conventional inspection methods have used multiple ultrasonic transducers for inspection of the same component, each transducer optimized for a relatively narrower depth zone.

Figure 1:
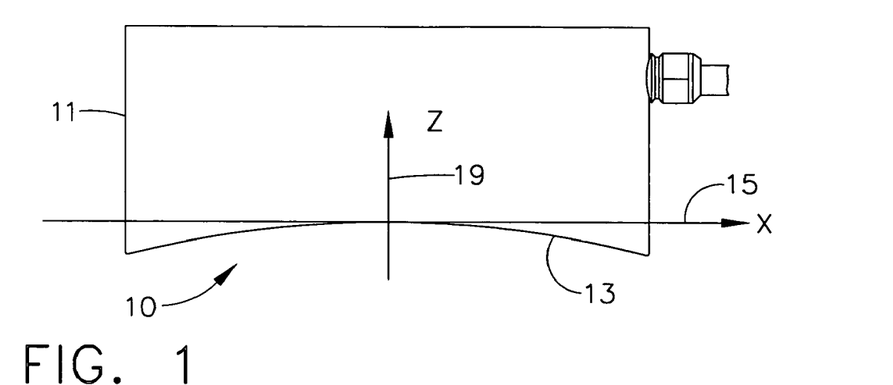
FIG. 1 is a cross-sectional view of an ultrasonic phased array transducer assembly in accordance with the present invention showing a housing and an ultrasonic phased array transducer.
Figure 2:
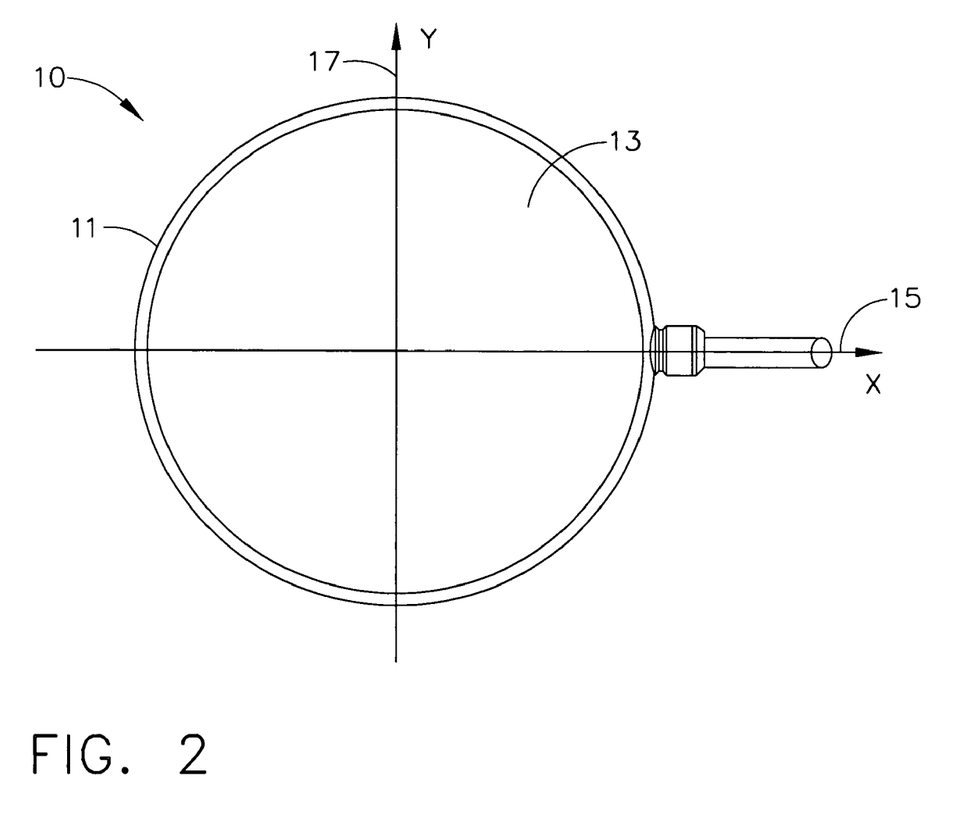
FIG. 2 is a view of the ultrasonic phased array transducer of FIG. 1 in accordance with the present invention.

In one embodiment of the present invention, shown in the views of FIGS. 1 and 2, an ultrasonic phased array transducer assembly 10 may include a metal housing 11 and an ultrasonic phased array transducer 13 forming a water-tight enclosure. The ultrasonic phased array transducer 13 may be fabricated by bonding together a plurality of piezo elements (not shown), for example, each piezo element formed from a piezoelectric or piezo-composite material. The physical configuration of the ultrasonic phased array transducer 13 may best be described with reference to a Cartesian coordinate system having an X-axis 15, a Y-axis 17, and a Z-axis 19 with the coordinate system origin located at the center of the surface of the ultrasonic phased array transducer 13.

The shape of the ultrasonic phased array transducer 13 is generally circular when viewed along the Z-axis as shown in FIG. 2, and is generally arc-shaped when intersected by the X-Z plane as shown in FIG. 1, such that an elliptical aperture is produced for the inspection of a solid cylindrical object, such as a titanium billet, located below the X-Y plane. In particular, the elliptical surface of the ultrasonic phased array transducer 13 is designed to produce a circular inspection spot at selected depths within such cylindrical objects.

Figure 3:
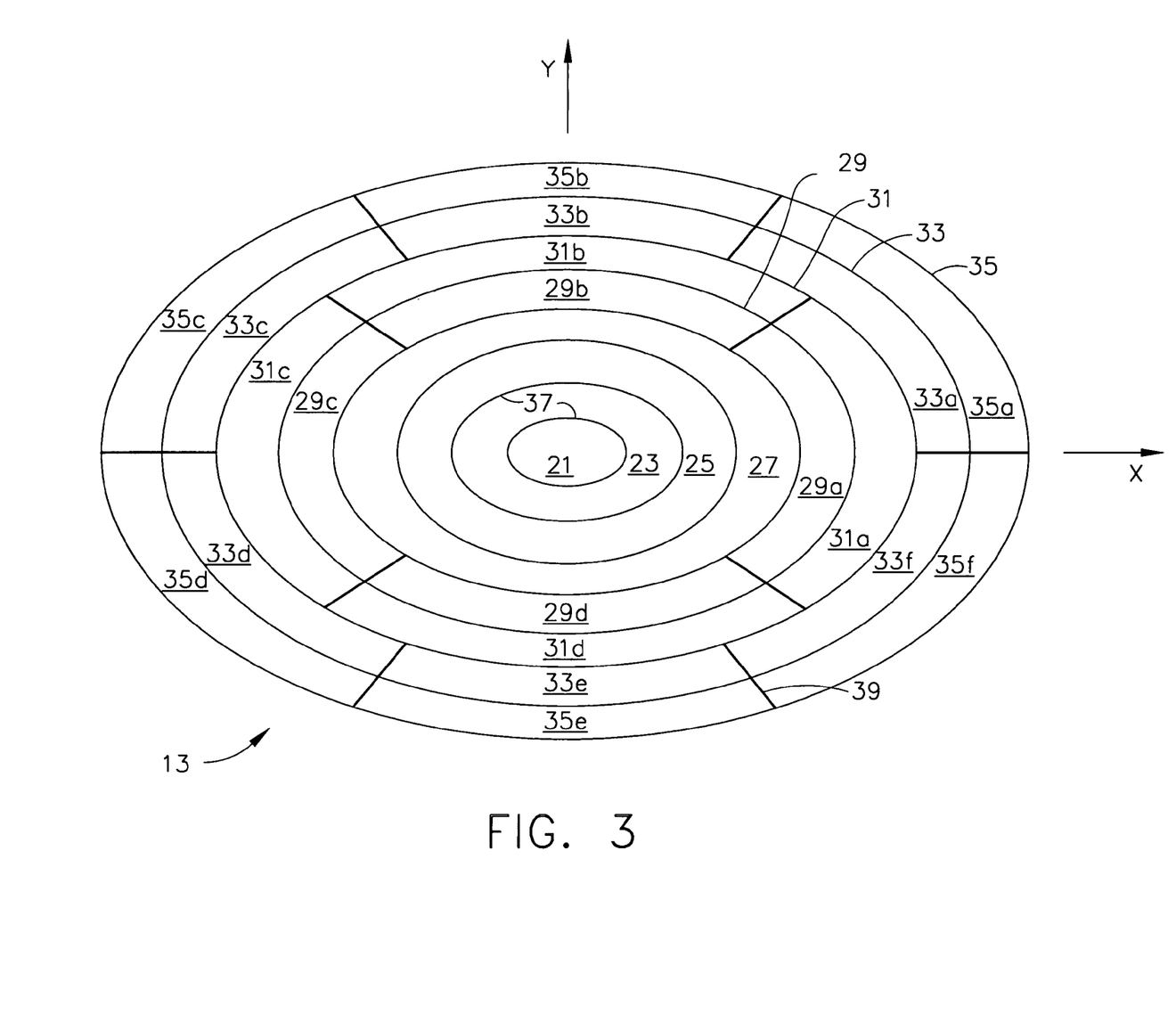
FIG. 3 is a more detailed view of the ultrasonic phased array transducer of FIG. 2.

As shown in FIG. 3, when the surface of the ultrasonic phased array transducer 13 is flattened and projected onto the X-Y plane, the surface has a generally elliptical shape. The ultrasonic phased array transducer 13 may include a substantially elliptical non-planar central component and a plurality of concentric elliptical annular components. It should be understood that, for clarity of illustration and for succinctness in generally describing the novel features of the present invention, the ultrasonic phased array transducer 13 is shown as having only seven elliptical components enclosing a central component. However, the invention is not so limited and may comprise a much greater number of components, as explained in greater detail below.

The non-planar central component in the ultrasonic phased array transducer 13 may comprise a generally elliptical piezo central element 21. A piezo ring element 23, which may be generally in the shape of an elliptical ring, may enclose the piezo central element 21. There may be a nominal radial spacing of approximately 10- to 500 -microns between the piezo central element 21 and the piezo ring element 23. The 10- to 500-micron spacing may be filled with a layer of composite material 37, such as a bonding agent used in the fabrication of ultrasonic transducers.

An elliptical piezo ring element 25 may enclose the piezo ring element 23. There may be an approximately 10- to 500-micron layer of composite material 37 between the piezo ring element 23 and the piezo ring element 25. An elliptical piezo ring element 27 may enclose the piezo ring element 25. There may also be an approximately 10- to 500-micron layer of composite material 37 between the piezo ring element 25 and the piezo ring element 27.

The sizes of the piezo central element 21 and each of the piezo ring elements 23–27 can be obtained using certain design criteria. In the embodiments of present invention, the ultrasonic phased array transducer 13 is designed to have the minimum number of transducer components by using piezo elements of varying active areas. In comparison, a conventional ultrasonic transducer design may specify that the active areas of the transducer components have approximately the same value so as to limit the variation among signals sent to and received from the transducer components. In the present invention, however, the respective areas of the transducer piezo elements are not so limited, but may have different values within a predetermined range specified as $A_{min} \leq area \leq A_{max}$. In the disclosed embodiments, signal variation is mitigated by the use of impedance matching circuitry in the signal lines to account for the variation in the active areas of the respective piezo elements, as described in greater detail below.

When the ultrasonic phased array transducer 13 is used for transmitting a signal, one or more of the piezo central element 21 and the piezo ring elements 23–27 are fired or excited by means of electrical channels provided between each piezo element and control electronics (see FIG. 4, below). Timing sequence and intervals for the excitation of the piezo central element 21 and the piezo ring elements 23–27 can be determined by means of a Focal Law calculation, as well known in the relevant art, to produce a specific spot size and shape at a depth within an object being ultrasonically inspected.

A sectored piezo ring 29 may enclose the piezo ring element 27 and may further comprise four piezo sector elements 29a–d forming a segmented elliptical ring as shown. There may be an approximately 10- to 500-micron layer of composite material 39 between adjacent piezo sector elements, such as between the piezo sector element 29a and the piezo sector element 29d, for example. A sectored piezo ring 31 may enclose the sectored piezo ring 29 and may comprise four piezo sector elements 31a–d, as shown, with an approximately 10- to 500-micron layer of composite material 39 between adjacent piezo sector elements. In alternative embodiments, the sectored piezo rings 29 and 31 may comprise two, six, eight, or more piezo sector elements instead of four as shown.

A sectored piezo ring 33 may enclose the sectored piezo ring 31 and may comprise six piezo sector elements 33a–f, as shown. There may be an approximately 10- to 500-micron layer of composite material 39 between adjacent piezo sector elements, such as between the piezo sector element 33e and the piezo sector element 33f, for example. A sectored piezo ring 35 may enclose the sectored piezo ring 33 and may comprise six piezo sector elements 35a–f, as shown, with an approximately 10- to 500-micron layer of composite material 39 between adjacent piezo sector elements. In alternative embodiments, the sectored piezo rings 33 and 35 may comprise two, four, eight, or more piezo sector elements instead of the six as shown.

It should be understood that, while the above-described embodiment includes a piezo central element, three concentric piezo ring elements, two concentric sectored piezo rings with four piezo sector elements, and two concentric sectored piezo rings with six piezo sector elements, the present invention is not limited to this particular configuration and more or fewer piezo ring elements and sectored piezo rings can be specified, including the use of sectored piezo rings having a number of piezo sector elements other than four or six as shown in FIG. 3.

Figure 4:
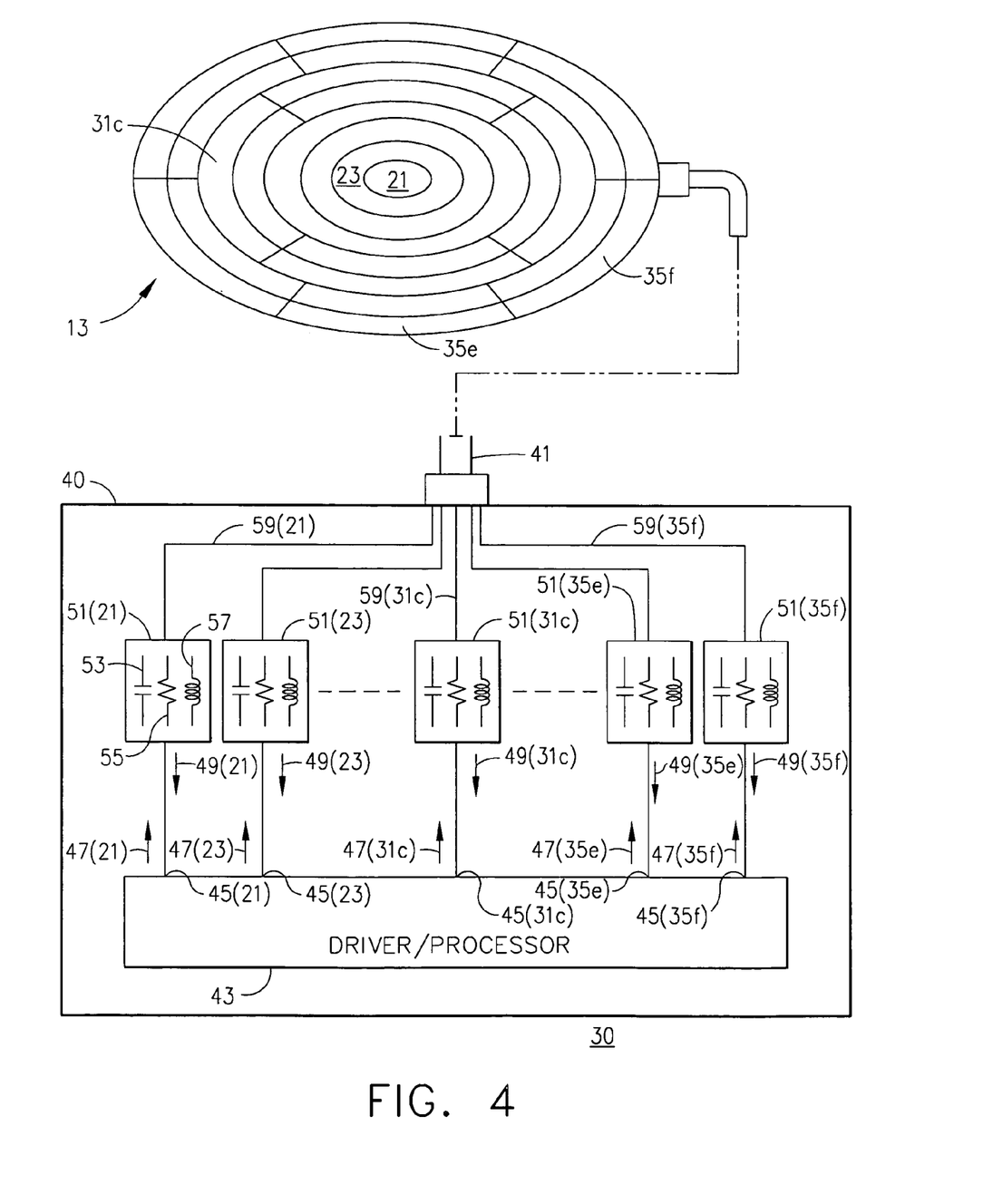
FIG. 4 is a diagrammatical representation of an ultrasonic phased array transducer system in accordance with the present invention showing the ultrasonic phased array transducer of FIG. 3, a transducer control, a signal/power cable, and impedance matching circuits on electrical channels connecting the ultrasonic phased array transducer and the transducer control.

The ultrasonic phased array transducer 13 may be connected to a transducer control 40 via a signal/power cable 41 to form an ultrasonic phased array transducer system 30, as shown in FIG. 4. The signal/power cable 41 provides a plurality of electrical channels 59(21) through 59(35f) between a multi-channel driver/processor 43 in the transducer control 40 and each transducer piezo element in the ultrasonic phased array transducer 13.

The driver/processor 43 includes a plurality of input/output ports 45(21), 45(23), ..., 45(31c), ..., 45(35e), and 45(35f) for the respective transducer piezo elements—the piezo central element 21, the piezo ring elements 23–27, the piezo sector elements 29a–d, the piezo sector elements 31a–d, the piezo sector elements 33a–f, and the piezo sector elements 35a–f—in the ultrasonic phased array transducer 13. During an illumination operation of the ultrasonic phased array transducer 13, one or more excitation signals 47(21), 47(23), ..., 47(31c), ..., 47(35e), and 47(35f) may be sent from one or more of the input/output ports 45(21), 45(23), ..., 45(31c), ..., 45(35e), and 45(35f) to one or more of the piezo central element 21, the piezo ring elements 23–27, the piezo sector elements 29a–d, the piezo sector elements 31a–d, the piezo sector elements 33a–f, and the piezo sector elements 35a–f in the ultrasonic phased array transducer 13.

During a sensing operation performed using the ultrasonic phased array transducer 13, one or more electrical waveform signals 49(21), 49(23), ..., 49(31c), ..., 49(35e), and 49(35f) may be received from one or more of the piezo central element 21, the piezo ring elements 23–27, the piezo sector elements 29a–d, the piezo sector elements 31a–d, the piezo sector elements 33a–f, and the piezo sector elements 35a–f at one or more of the respective input/output ports 45(21), 45(23), ..., 45(31c), ..., 45(35e), and 45(35f) in the ultrasonic phased array transducer 13.

The transducer control 40 provides piezo element impedance matching for the excitation signals 47(21), 47(23), ..., 47(31c), ..., 47(35e), and 47(35f) and for the waveform signals 49(21), 49(23), ..., 49(31c), ..., 49(35e), and 49(35f), as explained in greater detail below. A piezo element impedance matching circuit 51(21) may be provided in the electrical channel 59(21) between the input/output port 45(21) in the driver/processor 43 and the piezo central element 21 in the ultrasonic phased array transducer 13. The piezo element impedance matching circuit 51(21) may comprise one or more of a capacitive element 53, a resistive element 55, and an inductive element 57 forming an impedance matching circuit as is well known in the art so as to match the electrical characteristics of the piezo central element 21 to the input/output port 45(21).

That is, the electrical characteristics of the piezo element impedance matching circuit 51(21) are selected such that an electrical transducer piezo element load $Imp_{45(21)}$ "seen" by the input/output port 45(21) lies within a predetermined range of impedance values, that is $Imp_{min} \leq Imp_{45(21)} \leq Imp_{max}$, where $Imp_{min}$ and $Imp_{max}$ are design parameters. The electrical characteristics of the piezo element impedance matching circuit 51(21), for example, are thus determined at least in part by the value of the active area of the piezo central element 21.

A piezo element impedance matching circuit 51(23) may also be provided in the electrical channel 59(23) between the input/output port 45(23) in the driver/processor 43 and the piezo ring element 23 in the ultrasonic phased array transducer 13. The electrical characteristics of the piezo element impedance matching circuit 51(23) are selected such that an electrical load $Imp_{45(23)}$ seen by the input/output port 45(23) lies within the predetermined range of impedance values, that is $Imp_{min} \leq Imp_{45(23)} \leq Imp_{max}$.

Likewise, a piezo element impedance matching circuit 51(31c) may also be provided in the electrical channel 59(31c) between the input/output port 45(31c) and the piezo sector element 31c. An electrical load $Imp_{45(31c)}$ seen by the input/output port 45(31c) may lie within the predetermined impedance range such that $Imp_{min} \leq Imp_{45(31c)} \leq Imp_{max}$.

Similarly, piezo element impedance matching circuits 51(35e) and 51(35f) may be provided between the respective input/output ports 45(35e) and 45(35f) and the piezo sector elements 35e and 35f, where $Imp_{min} \leq Imp_{45(35e)} \leq Imp_{max}$, and $Imp_{min} \leq Imp_{45(35f)} \leq Imp_{max}$.

The transducer control 40 functions to send one or more of the excitation signals 47(21), 47(23), . . . , 47(31c), . . . , 47(35e), and 47(35f) to the ultrasonic phased array transducer 13, where the relative timing of each of the excitation signals 47(21), 47(23), . . . , 47(31c), . . . , 47(35e), or 47(35f) may be derived by means of the Focal Law calculation. For example, for near-surface inspection of the cylindrical object, only the piezo ring elements 21–27 may be excited. The sequential timing of the excitation of the piezo ring elements 21–27 may be specified so as to produce a desired spot size at a desired depth below the surface of the cylindrical object under inspection.

Figure 5:
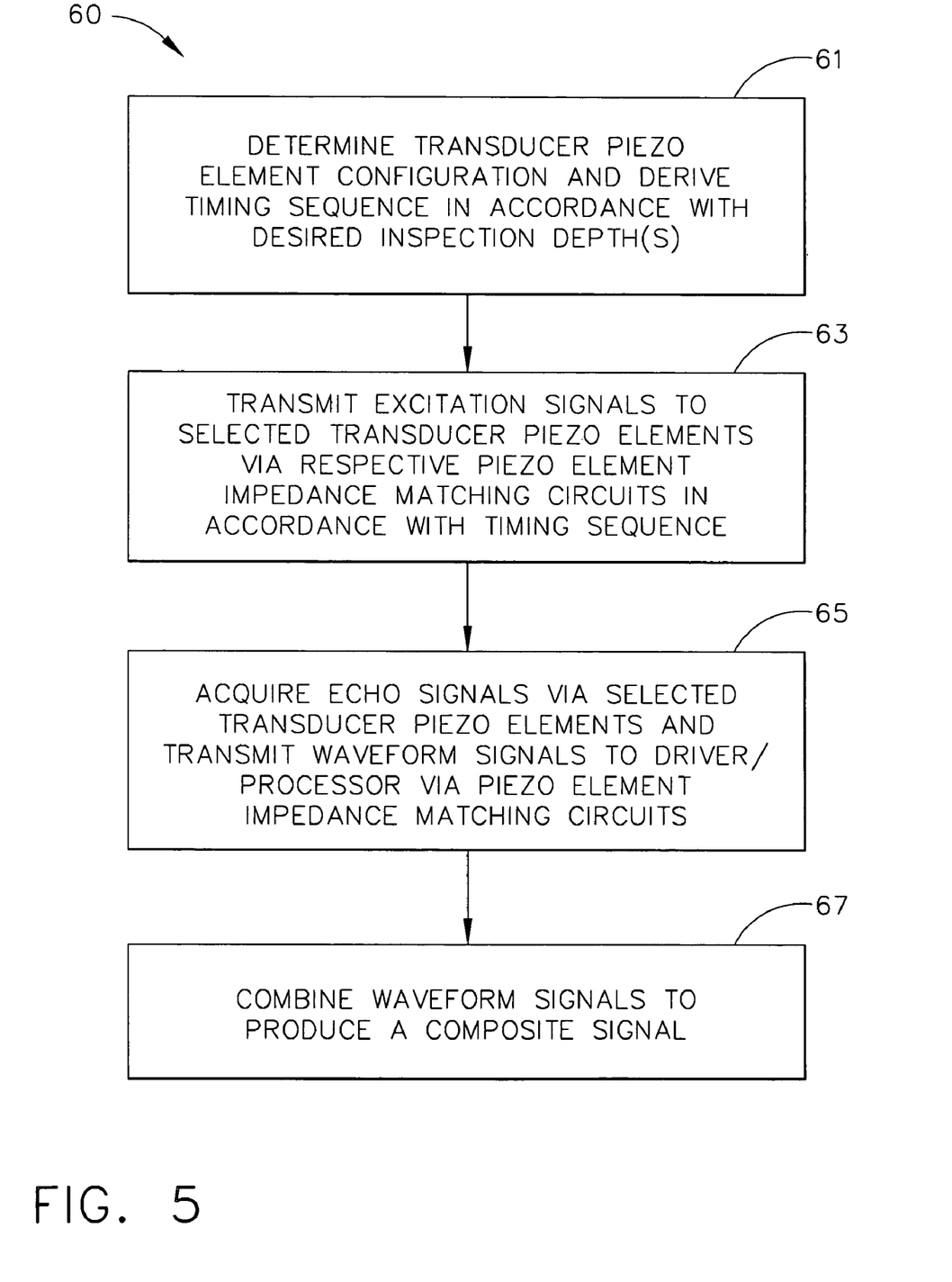
FIG. 5 is a flow diagram illustrating a process of detecting defects in a solid body by performing an ultrasonic inspection using the ultrasonic phased array transducer systems of FIGS. 4 and 9.

The process of detecting defects in a solid body by performing an ultrasonic inspection using the ultrasonic phased array transducer system 30, or other embodiment of the present invention, can be described with reference to a flow diagram 60 shown in FIG. 5. An inspection depth may be specified to determine the necessary transducer piezo element configuration. The appropriate transducer piezo elements may be selected for excitation in a timing sequence derived in accordance with the Focal Law calculations, at step 61. A plurality of excitation signals, such as excitation signals 47(21) through 47(27) for example, may be sent to the corresponding piezo central element 21 and the piezo ring elements 23–27 via the respective piezo element impedance matching circuits 51(21) through 51(27) and in accordance with the derived timing sequence so as to illuminate an object under inspection at the desired inspection depth, at step 63.

A plurality of "echo" signals are returned from the object under inspection to the piezo central element 21 and the piezo ring elements 23–27. The respective waveform signals 49(21) through 49(27) resulting from the echo signals are subsequently transmitted to the driver/processor 43 via the respective piezo element impedance matching circuits 51(21) through 51(27), at step 65. The piezo element impedance matching circuits 51(21) through 51(27) function to mitigate variations among the returned signals and to minimize destructive interference so as to preserve the quality of the overall signal. The plurality of waveform signals 49(21) through 49(27) are combined to produce a composite signal representing a portion of the view of the object under inspection at the specified depth, as is well-known in the relevant art, at step 67.

Figure 6:
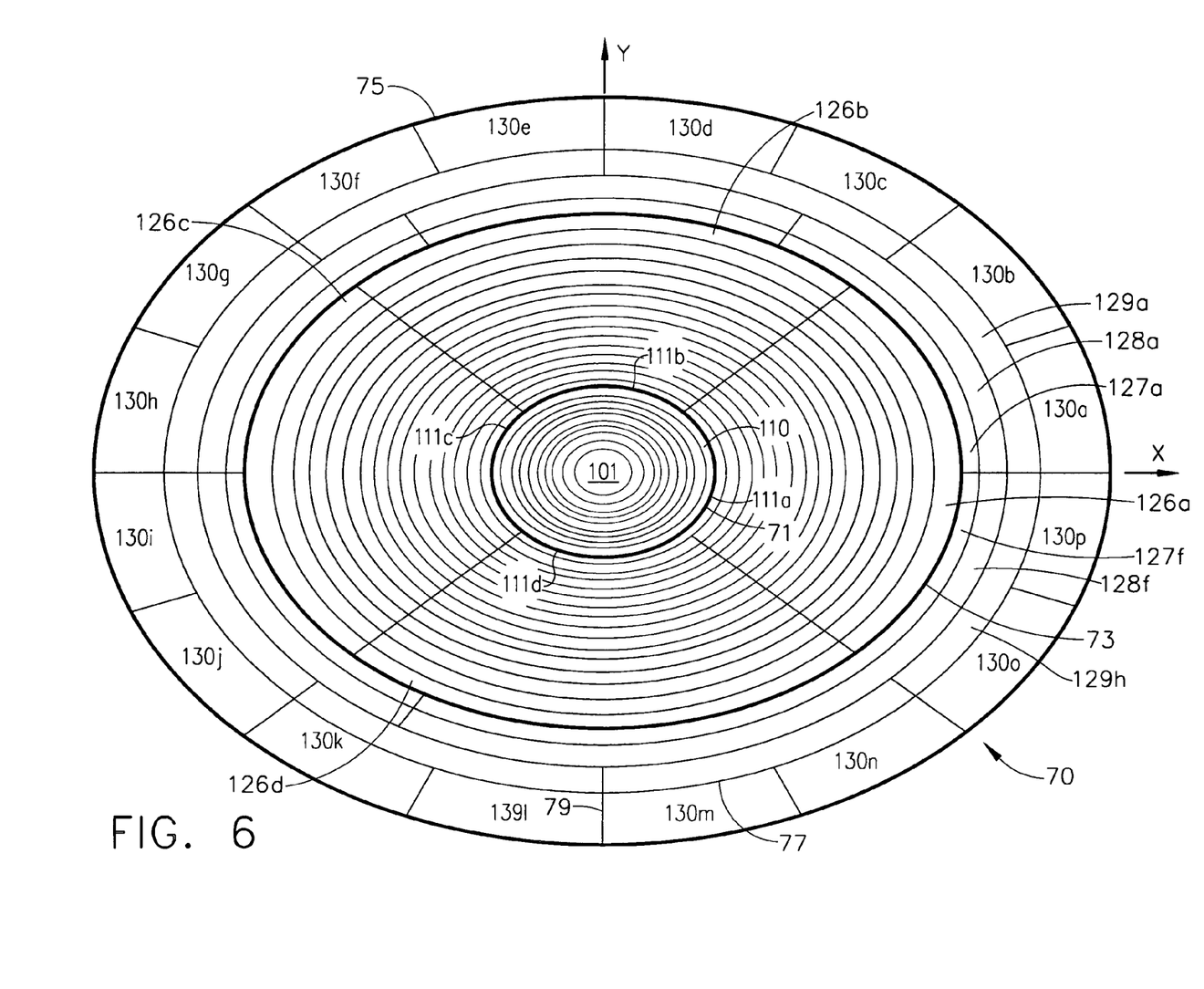
FIG. 6 is a diagram showing transducer components in a concentric array to form another embodiment of the ultrasonic phased array transducer of FIG. 3 in accordance with the present invention.

In another embodiment of the present invention, shown in FIG. 6, an ultrasonic phased array transducer 70 can be used to produce a tight focusing region of inspection (i.e., a spot size of approximately 40 mils or 1 mm) at depths ranging from 0.2 to 4.5 inches in, for example, an 8-inch diameter titanium billet (e.g., Ti-6AI-4V). The ultrasonic phased array transducer 70 may include an inner transducer piezo element group 71 comprising a piezo central element 101 and a plurality of nine (9) concentric piezo ring elements 102–110.

The geometric shape of the piezo central element 101, and the enclosing transducer components, can be determined by entering respective semi-axis values 'a' and 'b' into the well-known algebraic expression for an ellipse:

$$\frac{x^2}{a^2} + \frac{y^2}{b^2} = 1$$

where, for example, the piezo central element 101 has an X semi-axis value $a_{101}$ of approximately 4.81 mm, a Y semi-axis value $b_{101}$ of approximately 3.46 mm, and an area of approximately 52.3 mm$^2$. The parameters 'x' and 'y' provide the coordinate values of the outer edges of the respective elliptical rings and sectored rings. The semi-axis dimensions from the origin to the outer edges of the nine concentric elliptical piezo ring elements 102–110, intersecting the X- and Y-axes respectively, may have the approximate values listed in Table I, which also lists the areas corresponding to the piezo ring elements 102–110.

The ultrasonic phased array transducer 70 may also include an intermediate transducer piezo element group 73 comprising sixteen (16) elliptical sectored piezo rings 111 through 126 enclosing the inner transducer piezo element group 71. Each of the sectored piezo rings 111 through 126 may comprise four piezo sector elements, as exemplified by piezo sector elements 111a, 111b, 111c, 111d, 126a, 126b, 126c, and 126d (where piezo sector rings 112 through 125 disposed outside the sectored piezo ring 111 and inside the sectored piezo ring 126 are not labeled for clarity of illustration).

TABLE I

| Element | X semi-axis (mm) | Y semi-axis (mm) | Area (mm$^2$) |
|---|---|---|---|
| 102 | 6.73 | 4.84 | 50.2 |
| 103 | 8.18 | 5.88 | 48.6 |
| 104 | 9.46 | 6.80 | 51.1 |
| 105 | 10.42 | 7.50 | 43.2 |
| 106 | 11.70 | 8.42 | 64.1 |
| 107 | 12.83 | 9.23 | 62.2 |
| 108 | 14.11 | 10.15 | 78.1 |
| 109 | 15.39 | 11.07 | 85.5 |
| 110 | 16.83 | 12.11 | 105.1 |

The piezo sector elements 111a through 126a lying on the +X axis may subtend an elliptical arc of approximately 71.4°, that is from approximately 35.7° below the +X axis, at one edge of each piezo sector element 111a through 126a, to approximately 35.7° above the +X axis, at the other edge of each piezo sector element 111a through 126a. The piezo sector elements 111c through 126c lying on the –X axis may subtend an elliptical arc from approximately 35.7° above the –X axis, at one edge of each piezo sector element 111c through 126c, to approximately 35.7° below the –X axis, at the other edge of each piezo sector elements 111c through 126c. The piezo sector elements 111b through 126b and 111d through 126d may subtend an elliptical arc of approximately 108.6°.

The dimensions of the sectored piezo rings 111 through 126, as measured from the origin to the respective outer edges intersecting the X- and Y-axes, may have the approximate values listed in Table II, which also lists the approximate areas of each of the piezo sector elements in each listed sectored piezo ring.

The ultrasonic phased array transducer 70 may also include an outer transducer piezo element group 75 comprising elliptical sectored piezo rings 127, 128, 129, and 130 enclosing the intermediate transducer piezo element group 73. The sectored piezo ring 127 may comprise six (6) piezo sector elements 127a, 127b, 127c, 127d, 127e, and 127f; and the sectored piezo ring 128 may comprise six piezo sector elements 128a, 128b, 128c, 128d, 128e, and 128f.

The sectored piezo ring 127 has an X semi-axis value $a_{127}$ of approximately 53.71 mm, a Y semi-axis value $b_{127}$ of approximately 38.64 mm, and each piezo sector element 127a, 127b, 127c, 127d, 127e, and 127f may comprise an area of approximately 132.0 mm² with angular dimensions as listed in Table III, for a total area of approximately 792.0 mm² for the sectored piezo ring 127. The sectored piezo ring 128 may have an X semi-axis value $a_{128}$ of approximately 57.72 mm, a Y semi-axis value $b_{128}$ of approximately 41.52 mm, and each piezo sector element 128a, 128b, 128c, 128d, 128e, and 128f may comprise an area of approximately 168.2 mm² with angular dimensions (measured from the X-axis) as listed in Table III, for a total area of approximately 1009.2 mm² for the sectored piezo ring 128. The piezo sector elements 127a-f and 128a-f subtend elliptical arcs of approximately 51.3° or 77.5°.

TABLE II

| Element | X semi-axis (mm) | Y semi-axis (mm) | Sector Area (mm²) |
| --- | --- | --- | --- |
| 111 | 18.28 | 13.15 | 28.6 |
| 112 | 19.88 | 14.30 | 34.6 |
| 113 | 21.48 | 15.46 | 37.5 |
| 114 | 23.09 | 16.61 | 40.4 |
| 115 | 24.85 | 17.88 | 47.8 |
| 116 | 26.77 | 19.26 | 56.1 |
| 117 | 28.54 | 20.53 | 55.1 |
| 118 | 30.62 | 22.03 | 69.7 |
| 119 | 32.71 | 23.53 | 74.6 |
| 120 | 34.79 | 25.03 | 79.5 |
| 121 | 37.03 | 26.64 | 91.1 |
| 122 | 39.44 | 28.37 | 103.9 |
| 123 | 41.84 | 30.10 | 110.5 |
| 124 | 44.41 | 31.95 | 125.0 |
| 125 | 47.29 | 34.02 | 149.5 |
| 126 | 50.34 | 36.22 | 168.1 |

TABLE III

| Piezo Element | Angular Dimension From | To |
| --- | --- | --- |
| 127a, 128a | 0.0° | 51.3° |
| 127b, 128b | 51.3° | 128.8° |
| 127c, 128c | 128.8° | 180.0° |
| 127d, 128d | 180.0° | 231.3° |
| 127e, 128e | 231.3° | 308.7° |
| 127f, 128f | 308.7° | 360.0° |

The sectored piezo ring 129 may have an X semi-axis value $a_{129}$ of approximately 62.69 mm, a Y semi-axis value $b_{129}$ of approximately 45.10 mm. The sectored piezo ring 129 may further comprise eight (8) piezo sector elements 129a, 129b, 129c, 129d, 129e, 129f, 129g, and 129h, where each piezo sector element 129a-129h may have an area of approximately 169.0 mm², with an arc dimension of approximately 35.7° or 54.3° as listed in Table IV.

TABLE IV

| Piezo Element | Angular Dimension From | To |
| --- | --- | --- |
| 129a | 0.0° | 35.7° |
| 129b | 35.7° | 90.0° |
| 129c | 90.0° | 144.3° |
| 129d | 144.3° | 180.0° |
| 129e | 180.0° | 215.7° |
| 129f | 215.7° | 270.0° |
| 129g | 270.0° | 324.3° |
| 129h | 324.3° | 360.0° |

The sectored piezo ring 130 may have an X semi-axis value $a_{130}$ of approximately 71.98 mm and a Y semi-axis value $b_{130}$ of approximately 51.79 mm. The sectored piezo ring 130 may further comprise sixteen (16) piezo sector elements 130a through 130p, where each piezo sector element 130a–130p may have an area of approximately 176.9 mm², with elliptical arcs having angular dimensions of 16.6°, 19.1°, 24.4° and 29.9° as listed in Table V.

TABLE V

| Piezo Element | Angular Dimension From | To |
| --- | --- | --- |
| 130a | 0.0° | 16.6° |
| 130b | 16.6° | 35.7° |
| 130c | 35.7° | 60.1° |
| 130d | 60.1° | 90.0° |
| 130e | 90.0° | 119.9° |
| 130f | 119.9° | 144.3° |
| 130g | 144.3° | 163.4° |
| 130h | 163.4° | 180.0° |
| 130i | 180.0° | 196.6° |
| 130j | 196.6° | 215.7° |
| 130k | 215.7° | 240.1° |
| 130l | 240.1° | 270.0° |
| 130m | 270.0° | 299.9° |
| 130n | 299.9° | 324.3° |
| 130o | 324.3° | 343.4° |
| 130p | 343.4° | 360.0° |

Generally, the area of each transducer piezo element in the ultrasonic phased array transducer 70 may have a value lying within the range of about 25 to 180 mm². That is, the ratio of the piezo element having the largest area to the piezo element having the smallest area is about 7.2 to 1.

There may be an approximately 10- to 500-micron layer of composite material 77 between adjacent sectored piezo rings, such as between the sectored piezo rings 129 and 130. There may also be an approximately 10- to 500-micron layer of composite material 79 between adjacent piezo sector elements, such as between the piezo sector element 130l and the piezo sector element 130m.

Figure 7:
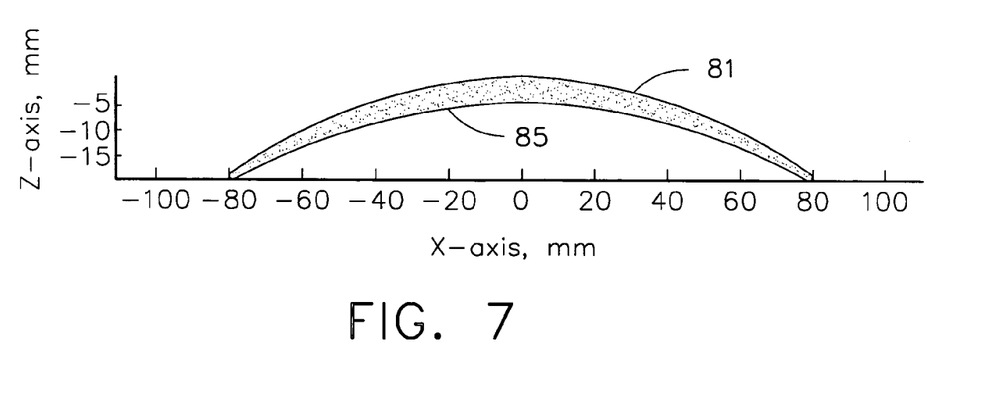
FIG. 7 is a side view of the ultrasonic phased array transducer of FIG. 6.
Figure 8:
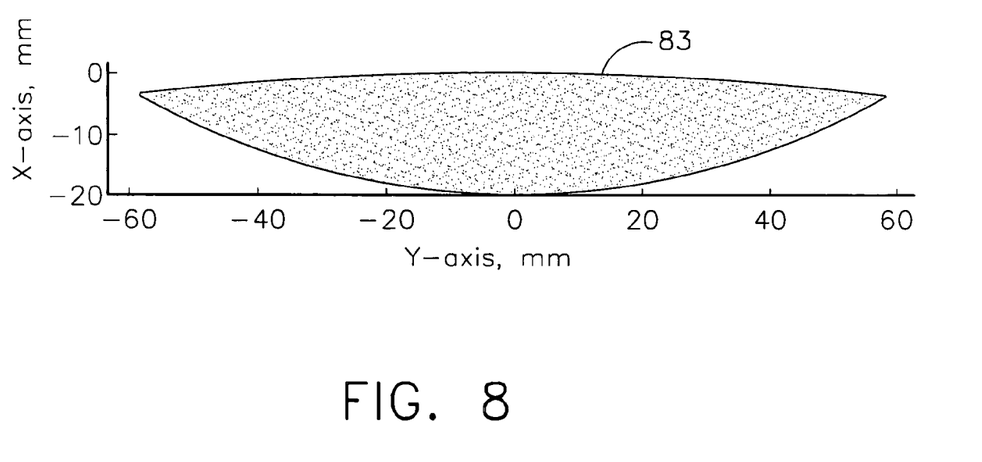
FIG. 8 is an end view of the ultrasonic phased array transducer of FIG. 6.

The ultrasonic phased array transducer 70 may have a cross-sectional arc shape 81 at an intersecting X–Z plane, as shown in the side view of FIG. 7, and a bowed shape 83 in the Y–Z plane, as shown in the end view of FIG. 8. As can be seen from the dimensions provided on the XZ-axes and the XY-axes provided in FIGS. 7 and 8, the ultrasonic phased array transducer 70 may be approximately 160 mm wide, as measured along the X-axis, approximately 120 mm wide, as measured along the Y-axis, and have a depth of approximately 20 mm as measured along the Z-axis. The object under inspection (not shown) can be positioned proximate a concave surface 85 of the ultrasonic phased array transducer 70 during the process of performing the ultrasonic inspection described above in the flow diagram 60 of FIG. 5.

Figure 9:
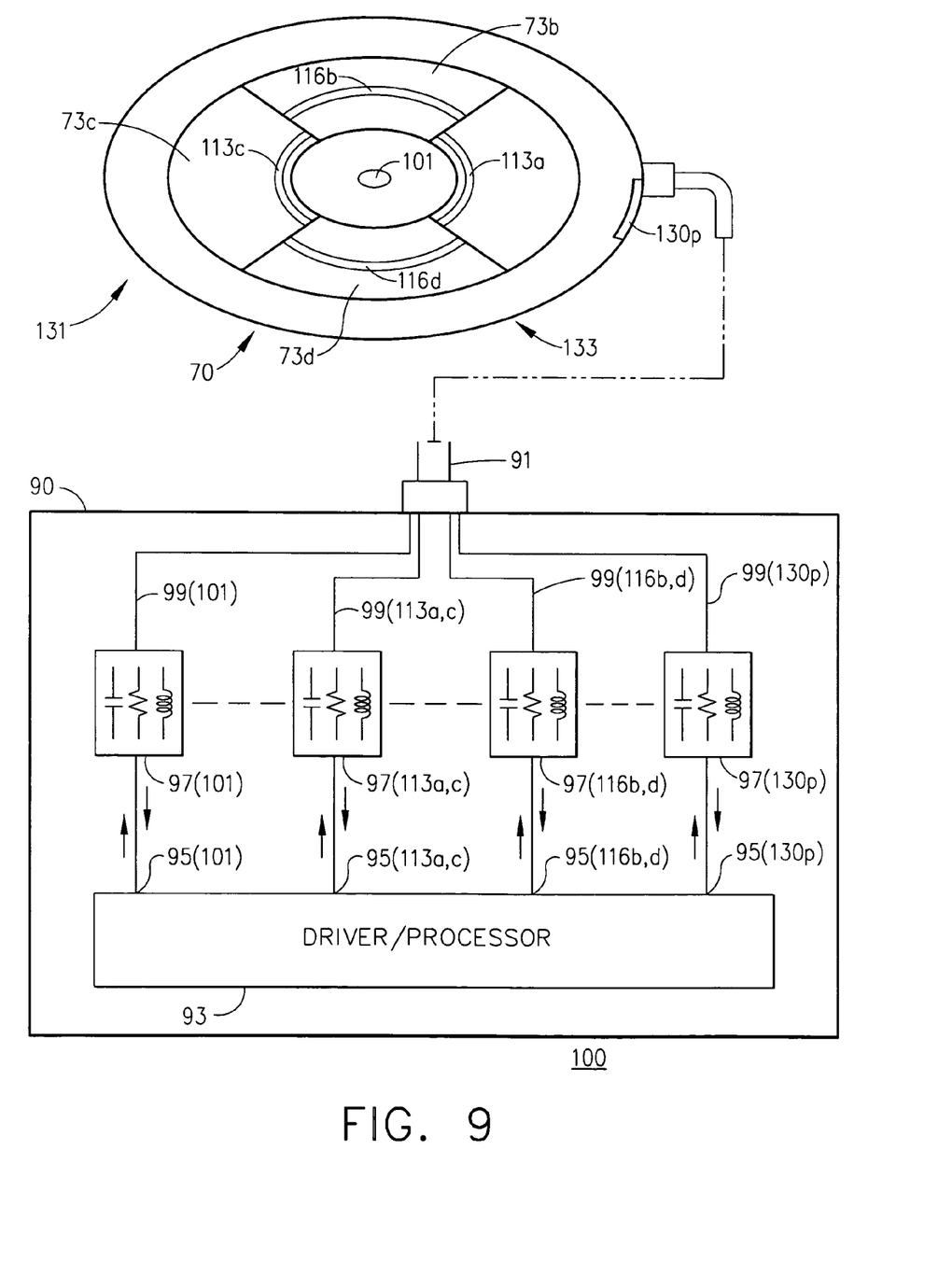
FIG. 9 is another embodiment of the ultrasonic phased array transducer system of FIG. 4 in accordance with the present invention.

In another embodiment of the present invention, the ultrasonic phased array transducer 70 may be secured to a housing (not shown) and may be connected to a transducer control 90 via a signal/power cable 91 to form an ultrasonic phased array transducer system 100, as shown in FIG. 9. The signal/power cable 91 may provide a plurality of electrical channels 99(101) through 99(130p) between a multi-channel driver/processor 93 in the transducer control 90 and each transducer piezo element in the ultrasonic phased array transducer 70. The driver/processor 93 may include a plurality of input/output ports, from an input/output port 95(101) electrically connected to the piezo central element 101 in the ultrasonic phased array transducer 70, for example, to an input/output port 95(130p) electrically connected to the piezo sector element 130p. Each channel 99(101) through 99(130p) may include a respective piezo element impedance matching circuit 97(101) through 97(130p) such that electrical loads $Imp_{99}(101)$ through $Imp_{99}(130p)$ seen by the input/output ports 95(101) through 95(130p) lie within the predetermined range of impedance values specified by the transducer designer. The center frequency for the ultrasonic phased array transducer 70 may be approximately 7.5 MHz.

In yet another embodiment, one or more opposing pairs of piezo sector elements may form an electrical element by being electrically connected to a common input/output port. The piezo sector elements 111a, 112a, . . . , 126a may define a transducer sector 73a, and the piezo sector elements 111c, 112c, . . . , 126c may define an opposing transducer sector 73c. The piezo sector elements 111b, 112b, . . . , 126b may define a transducer sector 73b, and the piezo sector elements 111d, 112d, . . . , 126d may define an opposing transducer sector 73d. The piezo sector element 113a in transducer sector 73a and the opposing piezo sector element 113c in the transducer sector 73c may thus be connected to a common input/output port 95(113a,c) in the driver/processor 93 to form a major axis electrical element 131. Similarly, the piezo sector element 116b in the transducer sector 73b and the opposing piezo sector element 116d in the transducer sector 73d may be connected to a common input/output port 95(116b,d) to form a minor axis electrical element 133.

The driver/processor 93 may provide up to 128 voltage channels and 32 timing channels, for example, for use with the ultrasonic phased array transducer 70 which comprises 110 transducer components. By combining the signals of opposed piezo sector elements, for example, the number of channels required in the driver/processor 93 can be reduced from the number of channels required if signals are not combined.

In another embodiment of the present invention, which can be described with reference to FIG. 5, a method for using an ultrasonic phased array transducer, such as the ultrasonic phased array transducer assembly 10 or the ultrasonic phased array transducer 70 for example, for detecting defects in a solid body may include selecting one or more transducer piezo elements and electrical elements in the ultrasonic phased array transducer assembly 10 or in the ultrasonic phased array transducer 70 for excitation in accordance with a desired inspection depth, such as an inspection depth of up to 4.5 inches in an 8-inch billet.

The method may further include the derivation of a timing sequence for the excited transducer piezo elements and electrical elements as a function of the desired inspection depth. Focal Law calculations may be used for selecting the excited transducer piezo elements and electrical elements as well as for determining the respective timing sequence, at step 61. With the transducer piezo elements and electrical elements selected, and with the timing sequence specified, one or more of the excitation signals may be transmitted to a respective one or more selected transducer piezo elements and electrical elements in accordance with the timing sequence, at step 63, where the excitation signals are transmitted via piezo element impedance matching circuits, such as the piezo element impedance matching circuits 51(21)–51(35f) for example.

One or more echo signals may be acquired via the selected transducer piezo elements and electrical elements, and the acquired echo signals may be transmitted as one or more waveform signals to a driver/processor, such as the driver/processor 43 or the driver/processor 93 for example, via the respective piezo element impedance matching circuits, at step 65. These echo signals may then be combined, as well-known in the relevant art, to produce a composite signal representative of an internal view of the solid body under inspection, at step 67.

Generally, impedance matching may be provided between ultrasonic probes, including phased array ultrasonic probes, and associated driver/processors such as used in performing ultrasonic inspections. See, for example the technical paper entitled, "*Ultrasonic Phased Array Inspection of Titanium Billets*," by Vincent Lupien and Fabrice Cancre, incorporated herein in entirety by reference. The technical paper discusses a phased-array transducer with equal-area transducer elements, where the transducer is impedance matched to a driver/processor using the same impedance-matching circuitry for each of the transducer elements. Because the areas of the transducer elements in the ultrasonic probe are of equal size, the impedance matching requirements do not vary from channel to channel. Thus, if an impedance-matching circuit on one channel includes discrete electrical components, each of the other channels would include the same discrete electrical components for impedance matching.

In contrast, as the ultrasonic phased array transducer 13 or 70 includes piezo elements having areas which vary from piezo element to piezo element, different piezo element impedance matching components may be required for different channels connecting piezo elements and electrical elements in the ultrasonic phased array transducer 13 or 70 with the respective driver/processor 43 or 93. It can be appreciated by one skilled in the relevant art that the disclosed method of using piezo elements and electrical elements with varying active areas on the face of a phased array probe allows a transducer designer to achieve certain design objectives that may be impractical with a conventional ultrasonic probe having equal-area elements.

Accordingly, the disclosed configurations utilize piezo element impedance matching circuitry to mitigate the variations in the impedance of the piezo elements and channel electrical characteristics as would otherwise be seen by the respective driver/processor 43 or 93. In order to achieve optimal performance of a phased array transducer assembly with such variable active area piezo and electrical elements, an impedance matching process is conducted to equalize electrical impedance by providing an impedance matching circuit specific to each piezo element and, when present, to each electrical element. This equalized impedance is typically the best match possible to the respective driver/processor 43 or 93. Where discrete components, such as the capacitive element 53, the resistive element 55, and the inductive element 57, are used in the impedance matching circuits, the electrical values of the respective components will generally vary from one piezo element impedance matching circuit to another piezo element impedance matching circuit.

Figure 10:
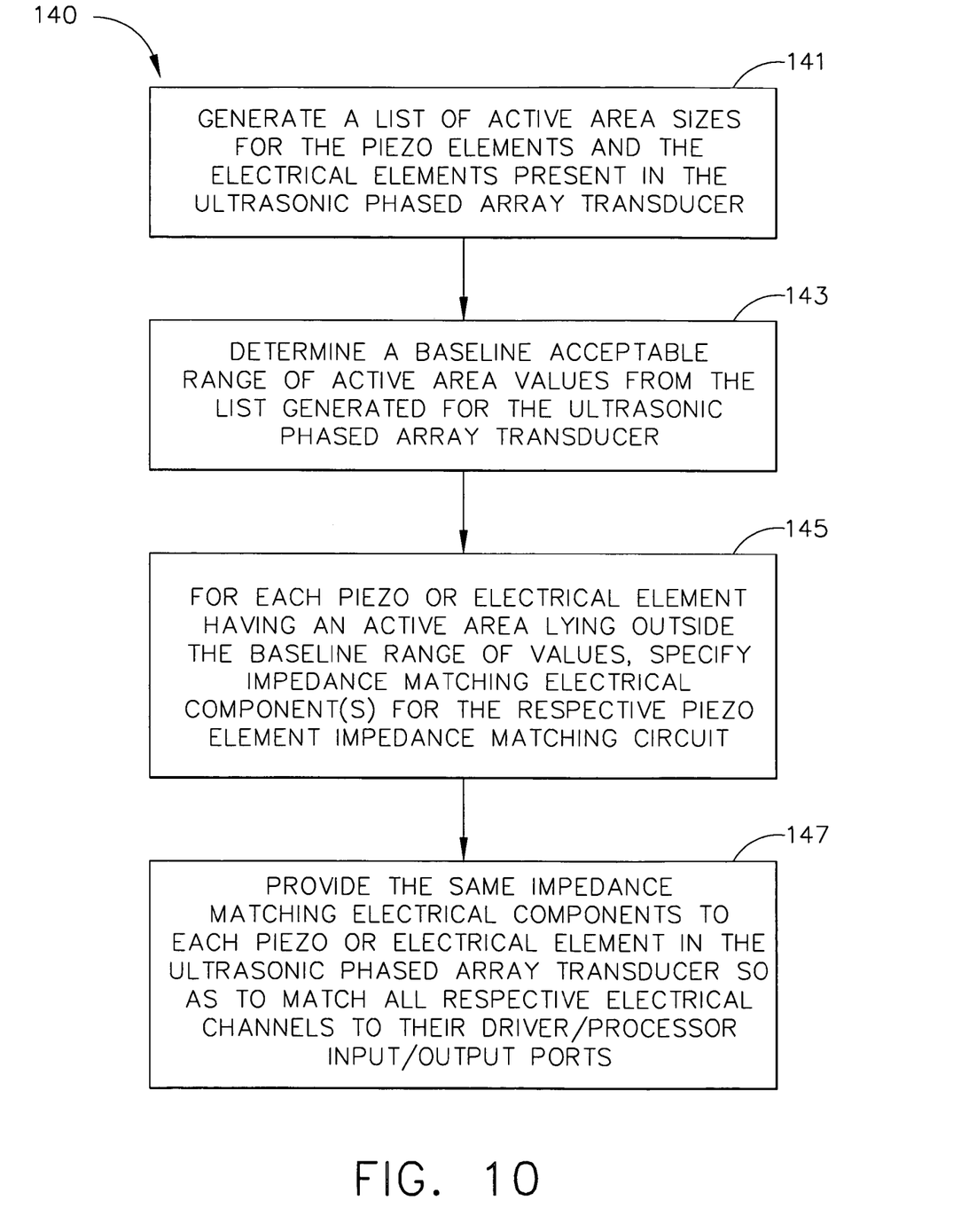
FIG. 10 is a flow diagram illustrating a process of specifying impedance matching components for electrical channels so as to match the electrical channels to their respective input/output ports.

In the present invention, an impedance matching method may follow the process shown in a flow diagram 140 shown in FIG. 10. A listing or histogram may be generated comprising the active area sizes or values of the various transducer elements and electric elements in the ultrasonic phased array transducer 13 or 70, at step 141. In the embodiment of FIG. 6, for example, a listing of active area values may include the range of 28.6 mm² to 168.1 mm². From this listing, a transducer designer can specify a baseline range of acceptable active area values, at step 143. In the embodiment of FIG. 6, for example, a range of acceptable values may be 90.0 mm² to 110.0 mm².

For each piezo element or electrical element having an active area lying outside the baseline range of acceptable values, a set of impedance matching electrical components can be derived for a particular impedance matching circuit in the respective electrical channel. In the embodiment of FIG. 6, for example, the piezo ring element 109 has an active area of 85.5 mm², which lies outside the acceptable, or preferred, range of 90.0 mm² to 110.0 mm² (see Table I). Accordingly, a piezo element impedance matching circuit 97(109) (not shown) in an electrical channel 99(109) (not shown) may comprise discrete electrical components functioning such that the impedance of the piezo ring element 109 seen by the input/output port 95(109) (not shown) in the driver/processor (shown in FIG. 9) lies within the acceptable range of 90.0 mm² to 110.0 mm². That is, piezo element impedance matching circuits function to correct for large variations in areas of piezo elements (i.e., piezo element areas having values lying outside the acceptable range of values). Referring again to Table I, the piezo ring element 110 has an active area of 105.1 mm², which lies inside the acceptable range of 90.0 mm² to 110.0 mm². Accordingly, a piezo element impedance matching circuit 97(110) (not shown) may not be required in a respective electrical channel 99(110) (not shown).

Steps 141 through 145 of the flow diagram 140 shown in FIG. 10 comprise the first phase of a two-phase process for providing impedance matching in the ultrasonic phased array transducer system 30 or 100. The first phase specifies impedance matching electrical components for the piezo element impedance matching circuits and, in effect, corrects the piezo element and the electrical element circuits such that all channels appear to be of substantially equal impedance at the respective driver/processor 43 or 93. This presents the ultrasonic phased array transducer 13 or 70 as an assembly comprising piezo and electrical elements of approximately equal active area.

In the second phase, step 147, each electrical channel of the ultrasonic phased array transducer 13 or 70 is similarly impedance-matched to the impedance of the respective driver/processor 43 or 93. This impedance matching process may take into consideration other electrical parameters which can affect the impedance in the design of the piezo element impedance matching circuit. In the embodiment of FIG. 6, for example, additional impedance matching components may be provided at the respective transducer elements 101 through 130p in the ultrasonic phased array transducer 70 so as to match the respective electrical channels 99(101) through 99(130p) to the input/output ports 95(101) through 95(130p).

For example, at step 145 each electrical channel 99(101) through 99(130p) may present an impedance of 43 ohms to the respective input/output ports 95(101) through 95(130p). At step 147, therefore, each electrical channel 99(101) through 99(130p) would then be similarly corrected, with the same impedance matching components at the respective transducer elements 101 through 130p, to bring the respective impedances of the electrical channels 99(101) through 99(130p) to approximately 50 ohms, for example.

It should be understood, of course, that the foregoing relates to exemplary embodiments of the invention and that modifications may be made without departing from the spirit and scope of the invention as set forth in the following claims.

We claim:

1. An ultrasonic phased array transducer system comprising: an ultrasonic phased array transducer having a piezo central element with an active area, a concentric piezo ring element enclosing said piezo central element, said piezo ring element having an active area greater than said piezo central element active area, a concentric sectored piezo ring enclosing said piezo ring element, said sectored piezo ring having first and second piezo sector elements, said sectored piezo ring further having an active area greater than said piezo ring element active area; a driver/processor with a plurality of input/output ports; a first electrical channel connecting said piezo central element to a first input/output port in said driver/processor, said first electrical channel including a first impedance matching circuit functioning to match electrical characteristics of said piezo central element to said first input/output port; a second electrical channel connecting said piezo ring element to a second input/output port in said driver/processor, said second electrical channel including a second impedance matching circuit functioning to match electrical characteristics of said piezo ring element to said second input/output port; and a third electrical channel connecting said piezo sector element to a third input/output port in said driver/processor, said third electrical channel including a third impedance matching circuit functioning to match electrical characteristics of said piezo sector element to said third input/output port.

2. The transducer system of claim 1 wherein said piezo central element comprises an elliptical shape.

3. The transducer system of claim 2 wherein said piezo central element comprises elliptical semi-axis dimensions of approximately 4.81 mm and approximately 3.46 mm.

4. The transducer system of claim 1 wherein said piezo central element comprises an area of approximately 52.3 mm².

5. The transducer system of claim 1 wherein said piezo ring element comprises an elliptical ring.

6. The transducer system of claim 5 wherein said piezo ring element comprises elliptical semi-axis dimensions of from approximately 4.84 mm to approximately 16.83 mm.

7. The transducer system of claim 1 wherein said piezo ring element comprises an area of from approximately 43.2 mm² to approximately 105.1 mm².

8. The transducer system of claim 1 wherein said sectored piezo ring comprises at least two piezo sector elements.

9. The transducer system of claim 8 wherein at least one said piezo sector element subtends an elliptical arc having an approximate value from the group consisting of the angles 16.6°, 19.1°, 24.4°, 29.9°, 35.7°, 51.3°, 54.3°, 71.4°, 77.5°, and 108.6°.

10. The transducer system of claim 1 wherein at least one said piezo sector element comprises an area of from approximately 28.6 mm² to approximately 176.9 mm².

11. The transducer system of claim 1 further comprising a layer of composite material disposed between at least one of said piezo central element and said piezo ring element, said piezo ring element and said sectored piezo ring, or adjacent piezo sector elements in one of said sectored piezo rings.

12. The transducer system of claim 11 wherein said layer of composite material is approximately 10 to 500 microns thick.

13. The transducer system of claim 1 wherein said driver/processor functions at an operating frequency of approximately 7.5 MHz.

14. The transducer system of claim 1 wherein two opposed piezo sector elements are in electrical communication with one of said input/output ports.

15. The transducer system of claim 1 wherein at least one of said piezo central element, said piezo ring element, and said piezo sector element comprises one of a piezoelectric material or a piezo-composite material.

16. An ultrasonic phased array transducer system comprising: a housing; an ultrasonic phased array transducer attached to said housing to form a water-tight assembly, said ultrasonic phased array transducer having a piezo central element, a plurality of concentric piezo ring elements enclosing said piezo central element, a plurality of concentric sectored piezo rings enclosing said plurality of piezo ring elements, each said sectored piezo ring having first and second piezo sector elements; a transducer control including a driver/processor having a plurality of input/output ports, a plurality of impedance matching circuits; a first electrical channel connecting said piezo central element to a first input/output port in said driver/processor, said first electrical channel including a first said impedance matching circuit functioning to match electrical characteristics of said piezo central element to said first input/output port; a second electrical channel connecting said piezo ring element to a second input/output port in said driver/processor, said second electrical channel including a second said impedance matching circuit functioning to match electrical characteristics of said piezo ring element to said second input/output port; and a third electrical channel connecting said piezo sector element to a third input/output port in said driver/processor, said third electrical channel including a third said impedance matching circuit functioning to match electrical characteristics of said piezo sector element to said third input/output port.

17. The ultrasonic phased array transducer system of claim 16 wherein said ultrasonic phased array transducer has a curved, generally elliptical surface.

18. An ultrasonic phased array transducer system comprising: an ultrasonic phased array transducer having a piezo central element, nine concentric elliptical piezo ring elements enclosing said piezo central element, twenty concentric sectored piezo rings enclosing said nine piezo ring elements, each said sectored piezo ring having at least four piezo sector elements; a driver/processor having a plurality of input/output ports; and a plurality of piezo element impedance matching circuits, each said piezo element impedance matching circuit disposed in an electrical channel between a said input/output port and a respective one of said piezo central element, said piezo ring elements, or said piezo sector elements.

19. The transducer system of claim 18 further comprising an approximately 10 to 500 microns thick layer of composite material disposed between adjacent said piezo ring elements, said piezo sector elements and said piezo central element.

20. An ultrasonic phased array transducer suitable for use with a multi-channel driver/processor for inspecting a solid object, said transducer comprising:
a piezo central element; and
a plurality of concentric elliptical piezo ring elements enclosing said piezo central element, said plurality of concentric elliptical piezo ring elements including a first piezo ring element having an area of approximately 43.2 mm$^2$, a second piezo ring element having an area of approximately 105.1 mm$^2$, and a third piezo ring element having an area in the range of approximately 43.2 mm$^2$ to approximately 105.1 mm$^2$.

21. The transducer of claim 20 further comprising a plurality of concentric sectored piezo rings enclosing said plurality of piezo ring elements, each said sectored piezo ring having four piezo sector elements, each said piezo sector element having an area of 28.6 mm$^2$, an area of approximately 168.1 mm$^2$, or an area of from approximately 28.6 mm$^2$ to approximately 168.1 mm$^2$.

22. The transducer of claim 20 further comprising a plurality of concentric sectored piezo rings enclosing said plurality of piezo ring elements,—each said sectored piezo ring comprising semi-axis dimensions of from approximately 13.15 mm to approximately 50.34 mm.

23. The transducer of claim 20 further comprising a plurality of concentric sectored piezo rings enclosing said plurality of piezo ring elements,—each said sectored piezo ring having six piezo sector elements, each said piezo sector element having an area of approximately 132.0 mm$^2$, an area of approximately 168.2 mm$^2$, or an area of from approximately 132.0 mm$^2$ to approximately 168.2 mm$^2$.

24. The transducer of claim 20 further comprising two sectored piezo rings having six piezo sector elements, said two sectored piezo rings enclosing said plurality of concentric elliptical piezo ring elements, each of said two sectored piezo rings comprising semi-axis dimensions of from approximately 38.64 mm to approximately 57.72 mm.

25. The transducer of claim 20 further comprising two sectored piezo rings having six piezo sector elements, said two sectored piezo rings enclosing said plurality of concentric elliptical piezo ring elements, each of said two sectored piezo rings having an area of from approximately 792.0 mm$^2$ to approximately 1009.2 mm$^2$.

26. The transducer of claim 20 further comprising a sectored piezo ring having eight piezo sector elements enclosing said plurality of concentric elliptical piezo ring elements, each said piezo sector element having an area of approximately 169.0 mm$^2$.

27. The transducer of claim 20 further comprising a sectored piezo ring having sixteen piezo sector elements enclosing said plurality of concentric elliptical piezo ring elements, each said piezo sector element having an area of approximately 176.9 mm$^2$.

28. An ultrasonic phased array transducer suitable for use with a multi-channel driver/processor for inspecting a solid object, said transducer comprising:
a piezo central element;
nine concentric piezo ring elements enclosing said piezo central element, each said piezo ring element having an area of from approximately 43.2 mm$^2$ to approximately 105.1 mm$^2$;
sixteen concentric sectored piezo rings enclosing said nine piezo ring elements, each of said sixteen sectored piezo rings having four piezo sector elements, each of said four piezo sector elements having an area of from approximately 28.6 mm$^2$ to approximately 168.1 mm$^2$;
two concentric sectored piezo rings enclosing said nine piezo ring elements, each of said two sectored piezo rings having six piezo sector elements, each of said six piezo sector elements having an area of from approximately 132.0 mm$^2$ to approximately 168.2 mm$^2$;
an elliptical sectored piezo ring having eight piezo sector elements enclosing said nine piezo ring elements, each of said eight piezo sector elements having an area of approximately 169.0 mm$^2$; and
an elliptical sectored piezo ring having sixteen piezo sector elements enclosing said nine piezo ring elements, each of said sixteen piezo sector elements having an area of approximately 176.9 mm$^2$.

29. The transducer of claim 28 wherein each of said four piezo sector elements comprises an elliptical arc of either approximately 71.420 or approximately 108.6°.

30. The transducer of claim 28 wherein each of said six piezo sector elements comprises an elliptical arc of either approximately 51.3° or approximately 77.5°.

31. The transducer of claim 28 wherein each of said eight piezo sector elements comprises an elliptical arc of either approximately 35.7° or approximately 54.3°.

32. The transducer of claim 28 wherein each of said sixteen piezo sector elements comprises an elliptical arc of approximately 16.6°, 19.1°, 24.40° or 29.9°.

33. A ultrasonic phased array transducer system comprising: an ultrasonic phased array transducer with a plurality of transducer piezo elements having a range of active area values; a driver/processor having a plurality of input/output ports; a plurality of electrical channels disposed between said plurality of transducer piezo elements and said plurality of input/output ports such that each said input/output port is in electrical communication with at least one said transducer piezo element; a baseline range of acceptable active area values derived from a listing of said active area values; and active area impedance matching circuitry for one or more of said electrical channels such that each said input/output port in electrical communication with a corresponding said transducer piezo element sees an active area value lying within said baseline range of acceptable area values.

34. The ultrasonic phased array transducer system of claim 33 wherein at least one of said plurality of transducer piezo elements comprises an active area having a value ranging from approximately 28.6 $mm^2$ to approximately 176.9 $mm^2$.

35. The ultrasonic phased array transducer system of claim 33 wherein adjacent said transducer piezo elements are separated by a layer of composite material approximately 10 to 500 microns thick.

36. The ultrasonic phased array transducer system of claim 33 wherein said driver/processor operates at a frequency of approximately 7.5 MHz.

* * * * *

UNITED STATES PATENT AND TRADEMARK OFFICE
CERTIFICATE OF CORRECTION

PATENT NO.       : 7,245,063 B2
APPLICATION NO.  : 10/987707
DATED            : July 17, 2007
INVENTOR(S)      : Vincent Lupien et al.

It is certified that error appears in the above-identified patent and that said Letters Patent is hereby corrected as shown below:

Column 17, line 3, "71.420" should be changed to --71.4°--;
Column 17, line 12, "24.40°" should be changed to --24.4°--.

Signed and Sealed this

Fourth Day of December, 2007

JON W. DUDAS
*Director of the United States Patent and Trademark Office*